United States Patent [19]

Iwasaki et al.

[11] Patent Number: 5,354,565
[45] Date of Patent: Oct. 11, 1994

[54] BIOCIDE ACTIVATOR

[75] Inventors: Tetsuji Iwasaki; Tadashi Moriyama; Yuichi Hioki, all of Wakayama, Japan

[73] Assignee: Kao Corporation, Tokyo, Japan

[21] Appl. No.: 868,349

[22] Filed: Apr. 15, 1992

[30] Foreign Application Priority Data

Apr. 17, 1991 [JP] Japan .................... 3-085281

[51] Int. Cl.$^5$ .................... A01N 55/04; A01N 33/12; A01N 59/00; A01N 59/26
[52] U.S. Cl. .................... 424/605; 424/600; 424/601; 424/602; 424/604; 424/606; 424/666; 424/713; 424/718; 514/492; 514/493; 514/557; 514/558; 514/559; 514/560; 514/574; 514/642; 514/643; 514/711; 504/151; 504/152; 504/153; 504/150
[58] Field of Search ............... 514/493, 642, 643, 492, 514/557, 558, 559, 560, 574, 711; 564/291; 424/650, 601, 602, 604, 605, 606, 666, 713, 718; 504/150, 151, 152, 153

[56] References Cited

U.S. PATENT DOCUMENTS

| | | | |
|---|---|---|---|
| 2,666,010 | 1/1954 | Stayner | 514/642 |
| 3,141,905 | 7/1964 | Longley | 562/66 |
| 3,657,451 | 4/1972 | Horne, Jr. | 514/493 |
| 4,424,233 | 1/1984 | Badmin et al. | 514/493 |
| 4,824,867 | 4/1989 | Smith et al. | 514/642 |
| 4,844,734 | 7/1989 | Iwasaki et al. | 504/330 |
| 4,929,628 | 5/1990 | McArthur et al. | 514/364 |
| 5,100,920 | 3/1992 | Iwasaki et al. | 514/642 |

FOREIGN PATENT DOCUMENTS

| | | |
|---|---|---|
| 0068399 | 1/1983 | European Pat. Off. |
| 0237764 | 9/1987 | European Pat. Off. |
| 2600494 | 12/1987 | France |
| 9115120 | 4/1989 | World Int. Prop. O. |

OTHER PUBLICATIONS

Database WPIL, Derwent Publications Ltd., Abstract accession No. 82-10964E, week 8206; & JP-A-56169615, Dec. 26, 1981.

Database WPIL, Derwent Publications Ltd., Abstract accession No. 90-111375, week 9015; & JP-A-2061174, Mar. 1, 1990.

Patent Abstracts of Japan, vol. 9, No. 112, May 16, 1985 & JP-A-60 004 112, Jan. 10, 1985.

Farm Chemicals Handbook 1987, Meister Publishing Co., Willoughby, Ohio, pp. 267-268.

Primary Examiner—Richard L. Raymond
Assistant Examiner—John D. Pak
Attorney, Agent, or Firm—Birch, Stewart, Kolasch & Birch

[57] ABSTRACT

A biocide composition comprising
(A) 1 to 50% by weight of a biocide, and
(B) 0.005–60% by weight of a biocide activator having the specific formula is provided. The biocide effect of a biocide can be enhanced with the use of an effective amount of a biocide activator.

7 Claims, No Drawings

BIOCIDE ACTIVATOR

BACKGROUND OF THE INVENTION

1. Field of the Invention

This invention relates to an agricultural and horticultural biocide activator. More particularly, it relates to an agricultural and horticultural biocide activator which has long-life, good effect in activating a biocide and does not have a harmful effect on or cause damage to farm products, crops or useful plants.

2. Description of the Background Art

In general, a quaternary ammonium salt has a strong biocide activation effect. Practical use of the quaternary ammonium salts in agriculture and horticulture, however, is extremely difficult because these compounds show strong harmful effects or cause damage to farm products, crops, or useful plants.

It is known that harmful effects or damage to plants are reduced by using an anion compound having 10 or more carbon atoms or a polymer, as a counter-ion of the quaternary ammonium salt. However, the quaternary ammonium salts which have a counter ion having 10 or more carbon atoms or a polymer are not easily dissolved into water. It has therefore been difficult to produce an aqueous biocide composition in a high concentration of the quaternary ammonium salt.

It would be desirable, therefore, to provide a biocide composition which gives excellent biocide activation effect and has no harmful effect or causes no damage to farm products, crops or useful plants.

SUMMARY OF THE INVENTION

Accordingly, it is an object of this invention to provide a biocide composition which gives an excellent biocidal effect.

This and other objects of the invention, as will be made more apparent by the following description, have been achieved by the use of a specific quaternary ammonium salt with a biocide. The resulting biocide composition gives excellent effect as a bactericide, insecticide, acaricide, herbicide and the like.

DETAILED DESCRIPTION OF THE INVENTION AND PREFERRED EMBODIMENTS

A biocide composition has been discovered which comprises:

(A) 1 to 50% by weight of a biocide and
(B) 0.005 to 60% by weight of a biocide activator having the formula (I)

$$\underset{R_2}{\overset{R_1}{\diagdown}} \underset{R_4}{\overset{\oplus}{N}} \underset{R_3}{\overset{R_3}{\diagup}} \quad X^{\ominus} \qquad (I)$$

wherein $R_1$ represents linear or branched alkyl, alkenyl, alkylarylpolyalkylenyl, alkylpolyoxyethylenyl, alkylpolyoxypropylenyl, acylaminoalkyl or acyloxyalkyl, each having 20 to 40 carbon atoms; $R_2$ and $R_3$ are independently selected from the group consisting of

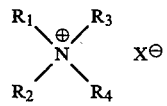

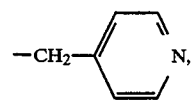

alkyl having 1 to 4 carbon atoms, and hydroxyalkyl having 2 to 4 carbon atoms, $R_4$ is selected from the group consisting of alkyl, alkylenyl, alkylpolyalkylenyl, alkylarylpolyalkylenyl, alkylpolyoxyethylenyl, alkylpolyoxypropylenyl, acylaminoalkyl and acyloxyalkyl each having 12 to 30 carbon atoms; and counter-ion $X^{\ominus}$ is an anion of a halogen acid, a phosphoric acid ester, a sulfuric acid ester, a carbonic acid ester, each having an alkyl group of 10 or fewer carbon atoms.

The biocidal effect of the biocide in said composition is enhanced by the use of an effective amount of a biocide activator having the formula (I).

$R_1$ and $R_4$ are described above. In this invention, the difference between the number of carbon atoms of $R_1$ and the number of carbon atoms of $R_4$ is relevant to the biocidal enhancement effect. The larger the difference in the number of carbon atoms between $R_1$ and $R_4$, the better the effect of the biocidal composition. If the difference in the number of carbon atoms between $R_1$ and $R_4$ is larger than two (2), the compounds having formula (I) have a biocidal activating effect.

Counter-anion $X^{\ominus}$ is halogen, e.g. $Cl^-$, $I^-$, $Br^-$, an anion residue of a phosphoric acid ester, a sulfuric acid ester, or a carbonic acid ester, each having an alkyl group of 10 or fewer carbon atoms.

Counter-anions having an alkyl group of 10 or fewer carbon atoms include alkyl phosphate, polyoxyethylene alkylphosphate, alkylsulfate, polyoxyethylene alkylsulfate, polyoxyethylene alkylphenylether phosphate, polyoxyethylene alkyl phenylether sulfate, alkylbenzene sulfate, naphthalene sulfate, alkylnaphthalene sulfate, polyoxyethylene tribenzylphenolether sulfate, polyoxyethylene tribenzylphenylether phosphate, and the like.

The method for preparing the quaternary ammonium compound of formula (I) is not limited. One example of the method is as follows: After introducing a group having 22 carbon atoms into alkylamine, the alkyl amine is quaternarized by using methyl chloride. The quaternary ammonium compound can also be obtained by hydroxyalkylation by using ethyleneoxide.

The quaternary ammonium compound having the formula (I) can be used in combination with other quaternary ammonium salts used for biocide compositions. The latter compound should be less than 50% based on a nitrogen atom of the quaternary ammonium compound of the invention.

The biocide activator of the present invention is used in combination with a biocide. The resulting biocide composition is applied to plants or soil. The amount of the biocide activator in the composition is 0.005 to 60% by weight, and preferably 0.1 to 40% by weight.

The biocide composition of the present invention can be prepared as an aqueous solution, a wettable powder, granules, powders, an emulsion, an oil composition, a paste or in any other form, according to conventional methods. Accordingly, biocidally acceptable additives, e.g. salts, surfactants, acids, thickening agents, carriers and the like, are used in combination with components (A) and (B), depending on the selected formulation.

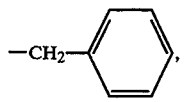

Examples of preferred salt additives includes metal salts of carboxylic acids, such as succinates, malonates, citrates, gluconates, and glutarates; metal salts of phosphoric acid compounds such as tripolyphosphates and hexametaphosphates; and inorganic salts such as $Na_2SO_4$ and $MgSO_4$. Any one of these salts, or a mixture thereof, may be employed.

As the surfactants, nonionic and anionic surfactants can be used. Preferred examples of the nonionic and/or anionic surfactants include nonionic surfactants such as polyoxyethylene (hereinafter simply referred to as POE) alkyl (carbon atom number: 6–22) ethers, POE alkyl (carbon atom number: 4–18) phenol ethers, polyoxypropylene polyoxyethylene (block or random) alkyl ethers, POE phenylphenol ethers, POE styrenated phenol ethers, and POE tribenzylphenol ethers; and anionic surfactants such as ligninsulfonate salts, alkylbenzenesulfonate salts, alkylsulfonate salts, POE alkylsulfonate salts, POE alkylphenyl ether sulfonate salts, POE alkylphenyl ether phosphate salts, POE phenylphenol ether sulfonate salts, POE phenylphenol ether phosphate salts, naphthalenesulfonate salts, naphthalenesulfonic acid/formalin condensate, POE tribenzylphenol ether sulfonate salts and POE tribenzylphenol ether phosphate salts. These surfactants can be used singly or in combination and are used in an amount of 0 to 30%, and preferably 1 to 15% by weight in the present composition.

Organic acids or inorganic acids may be added to the present composition. Preferred examples of these acids include acetic acid, butyric acid, capric acid, caproic acid, succinic acid, lactic acid, malonic acid, citric acid, gluconic acid, glutaric acid, phosphoric acid, tripolyphosphoric acid, hexametaphosphoric acid, methanesulfonic acid, sulfonic acid, hydrochloric acid, and nitric acid.

These acids can be used singly or in combination, and are used in an amount of 0 to 20%, and preferably 1 to 10% by weight in the present composition.

Natural, semi-synthetic or synthetic water-soluble thickeners may be used in the present composition. Preferred examples of the natural thickeners include xanthan gum and Zanflo originating from microorganisms, and pectin, gum arabic and guar gum originating from plants. Preferred examples of the semi-synthetic thickeners include methylated products, carboxylated products and hydroxyalkylated products of cellulose or starch derivatives (including methylcellulose, carboxymethylcellulose, and hydroxymethylcellulose) and sorbitol. Preferred examples of synthetic thickeners include polyacrylate salts, polymaleate salts, polyvinylpyrrolidone and EO adducts of pentaerythritol.

The above water-soluble thickeners may be used in the biocide composition in an amount of from approximately 0 to 3.0% by weight, and preferably from 0.05 to 0.5% by weight.

As the carrier, inorganic mineral salts and water-insoluble polymers may be employed. Preferred examples of the inorganic mineral salts include organic salt clays, talcs, bentonites, calcium carbonate, diatomaceous earths and white carbon. Preferred examples of the water-insoluble polymers include styrenesulfonic acid, 2-acrylamide, 2-methylpropanesulfonic acid, xylenesulfonic acid, naphthalenesulfonic acid, and polymers or salts thereof. Further, copolymers obtained by copolymerizing the above-mentioned polymer with a hydrophobic monomer such as alkyl acrylate, alkyl methacrylate, vinyl alkyl ethers, vinyl acetate, ethylene, propylene, butylene, butadiene, diisobutylene, vinyl chloride, vinylidene chloride, acrylonitrile or styrene; or a hydrophilic monomer such as acrylic acid, methacrylic acid, maleic acid, fumaric acid, maleic anhydride, vinyl alcohol, acrylamide, methacrylamide, diacetone acrylamide or N-vinylpyrrolidone may be employed.

The biocide activator of the present invention exhibits no adverse effect on various crops and thus can be applied safely.

Examples of preferred biocides for activation by the biocide activator of the present invention are as follows:

Examples of bactericides include Dithane Z-78 (zinc ethylenebis(dithiocarbamate)), Maneb (manganous ethylene- bis(dithiocarbamate)), Thiram (bis(dimethylthiocarbamyl)- disulfide), Manzeb (zinc/manganese ethylenebisdithio-carbamate), Bisdaithane (bisdimethyldithiocarbamoylzinc ethylenebisdithiocarbamate), benzimidazole derivatives such as Benomyl (methyl 1-(butylcarbamoyl)-2-benzimidazole-carbamate) and Thiophanate-methyl (1,2-bis(3-methoxy-carbonyl-2-thioureido) benzene), as well as Vinclozolin (3-(3,5-dichlorophenyl)-5-methyl-5-vinyl-1,3-oxazolidine-2,4-dione), Iprodione (3-(3,5-dichlorophenyl)-N-isopropyl-2,4-dioxoimidazolidine-1carboxamide), Procymidone (N-(3,5-dichlorophenyl)-1,2-dimethylcyclopropane-1,2-dicarboximide), Triazine (2,4-dichloro-6-(2-chloroanilino)-1,3,5-triazine), Triflumizole ((E)-4-chloro-$\alpha,\alpha,\alpha$-tritrifluoro-N-(1-imidazole-1-yl-2-propoxyethylidane)-O-toluidine), Metalaxyl (methyl N-(2 -methoxyacetyl)-N-(2,6-xylyl) -D, L-alaninate), Bitertanol (all-rac-1-(biphenyl-4-yloxy)-3,3 -dimethyl-1- (1H-1,2,4 -triazol-1-yl) butane-2 -ol) , Triadimefon (1-(4-chlorophenoxy)-3,3-dimethyl-1-(1H-1,2,4-triazol-1-yl)-2-butanone), Isoprothiolane (diisopropyl 1,3-dithiolane-2-ylidenemalonate), Daconil (tetrachloro-isophthalonitrile), Pansoil (5-ethoxy-3-trichloromethyl-1,2,4-thiadiazole), Rabcide (4,5,6,7-tetrachlorophthalolide), Kitazin P (0,0-diisopropyl-S-benzylthiophosphate), Hinosan (0-ethyl-S,S-diphenyl phosphorodithioate), Probenazol (3-allyloxy-1,2-benzisothiazole-1,1-dioxide) and Captan (N-trichloromethylthiotetrahydrophthalimide).

Examples of insecticides include pyrethroid insecticides, such as Fenvalerate ($\alpha$-cyano-3phenoxybenzyl 2-(4-chlorophenyl)-3-methylbutanoate) and Baythroid (cyano-4-fluoro-3-phenoxyphenylmethyl 3-(2,2-dichloroethenyl)-2,2-dimethylcyclopropane carboxylate); organophophorus insecticides, such as DDVP (dimethyl 2,2-dichlorovinyl phosphate), Sumithion (0,0-dimethyl-O-(3-methyl-4-nitrophenyl) thiophosphate), Malathion (S-(1,2-bis(ethoxycarbonyl)ethyl) dimethyl phosphorothioate), Dimethoate (dimethyl S-(N-methylcarbamoylmethyl) dithiophosphate), Elsan (S-$\alpha$-ethoxycarbonyl-benzyl) dimethyl phosphorothiolthionate) and Baycid (0,0-dimethyl 0-(3-methyl-4-methylthiophenyl) thiophosphate; carbamate insecticides such as Bassa (0-butylphenylmethylcarbamate), MTMC (m-tolyl methylcarbamate), Meobal (3,4-dimethylphenyl N-methylcarbamate) and NAC (1-naphthyl N-methylcarbamate); as well as Methomyl (S-methyl-N-((methylcarbamoyl) oxylthioacetimide) and Cartap (1,3-bis (carbamoylthio)-2-(N-N-dimethylamino)-propane hydrochloride.

Examples of acaricides include Smite (2-[2-p-tert-butylphenoxy) isopropoxy] isopropyl 2-chloroethyl sulfite), Acricide (2,4-dinitro-6-sec-butylphenyl methylacrylate), Chlormite (isopropyl 4,4-dichlorobenzilate), Akar (ethyl 4,4-dichlorobenzilate), Kelthane (1,1-bis(p-chlorophenyl)-2,2,2-trichloroethanol), Citrazon (ethyl 0-benzoyl-3-chloro-2,6-dimethoxybenzohydroxymate), Omite (2-(p-tert-butylphenoxy) cyclohexyl 2-propynyl sulfite), Osadan (hexakis(2-methyl-2-phenylpropyl) distannoxane), Hexithiazox (trans-5-(4-chlorophenyl)-N-cyclohexyl-4-methyl-2-oxothiazolidine-3-carboxamide) and Amitraz (3-methyl-1,5-bis (2,4-xylyl)-1,3,5-triazapenta-1,4-diene).

Examples of herbicides include Stam (3,4-dichloropropionanilide), Saturn (S-(4-chlorobenzyl) N,N-diethylthiocarbamate), Glyphosate (N-(phosphonomethyl)-glycine, isopropylamine salt), DCMU (3-(3,4-dichlorophenyl)-1,1-dimethylurea) and Glamoxone (1,1-dimethyl-4,4'-dipyridium dichloride).

Further, plant growth regulators such as MH (maleic acid hydrazide) and Ethrel (2-chloroethylphosphonic acid) may be employed.

The biocide composition of this invention may further contain one or more plant growth regulators, fertilizers and/or preservatives.

The biocide activator of the present invention may be added to each of the aforesaid compositions and formulated. Alternately, it may be diluted in use. The effect of suppressing resistance to biocides, according to the present invention, may be achieved by employing each of these methods.

Although a precise mechanism for the effect of the biocide activator of the present invention, namely enhancing biocidal effects of suppressing biocide-resistance, is not yet clear, it is thought that the biocide activator of the present invention may be adsorbed by the cell membrane of bacterium, thereby disturbing its permeability. Alternatively, it may inhibit the activity of membrane-bound enzymes which are localized on the surface of the bacterium, thereby damaging the bacterium and reducing its resistance to biocides. A similar effect was also found to be produced in relation to insecticides and acaricides.

Other features of the invention will become apparent in the course of the following description of the exemplary embodiments which are given for illustration of the invention, and are not intended to be limiting thereof.

EXAMPLE

Table 1 shows the quaternary ammonium salts of the present invention and the comparative compound and Formulation Examples will be given thereafter.

TABLE 1

| Compound No. | Quaternary ammonium | Counter Ion |
|---|---|---|
| 1 | $CH_3-\overset{\overset{CH_3}{\mid}}{\underset{\underset{(CH_2)_{15}-CH_3}{\mid}}{N^{\oplus}}}-(CH_2)_{21}-CH_3$ | $Cl^{\ominus}$ |
| 2 | $CH_3-\overset{\overset{CH_3}{\mid}}{\underset{\underset{(CH_2)_{15}-CH_3}{\mid}}{N^{\oplus}}}-(CH_2)_{21}-CH_3$ | $CH_3(CH_2)_4COO^{\ominus}$ |
| 3 | $CH_3-\overset{\overset{CH_2}{\mid}}{\underset{\underset{(CH_2)_{19}-CH_3}{\mid}}{N^{\oplus}}}-(CH_2)_{15}-CH_3$ | $Cl^{\ominus}$ |
| 4 | $CH_3-\overset{\overset{CH_3}{\mid}}{\underset{\underset{(CH_2)_{15}-CH_3}{\mid}}{N^{\oplus}}}-(CH_2)_{27}-CH_3$ | $Cl^{\ominus}$ |
| 5 | $CH_3-\overset{\overset{CH_3}{\mid}}{\underset{\underset{(CH_2)_{13}-CH_3}{\mid}}{N^{\oplus}}}-(CH_2)_{21}-CH_3$ | $CH_3SO_3^{\ominus}$ |
| Comparative Compound 1 | $CH_3(CH_2)_{11}-\overset{\overset{(CH_2)_{11}-CH_3}{\mid}}{\underset{\underset{CH_3}{\mid}}{N^{\oplus}}}-CH_3$ | $Cl^{\ominus}$ |
| Comparative Compound 2 | $CH_3(CH_2)_{7}-\overset{\overset{(CH_2)_{7}-CH_3}{\mid}}{\underset{\underset{CH_3}{\mid}}{N^{\oplus}}}-CH_3$ | $Cl^{\ominus}$ |

Formulation Example 1

| | |
|---|---|
| Compound No. 1 | 30 |
| | (parts by weight) |
| polyoxyethylene nonylphenyl ether (Emulgen 909, mfd. by Kao) | 5 |
| isopropyl alcohol | 65 |

Formulation Example 2

| | |
|---|---|
| Compound No. 2 | 30 |
| | (parts by weight) |
| polyoxyethylene nonylphenyl ether (Emulgen 909, mfd. by Kao) | 5 |
| isopropyl alcohol | 65 |

Formulation Example 3

| | |
|---|---|
| Compound No. 3 | 30 |
| | (parts by weight) |
| polyoxyethylene nonylphenyl ether (Emulgen 909, mfd. by Kao) | 5 |
| isopropyl alcohol | 65 |

Formulation Example 4

| | |
|---|---|
| Compound No. 4 | 30 |
| | (parts by weight) |
| polyoxyethylene nonylphenyl ether (Emulgen 909, mfd. by Kao) | 5 |
| isopropyl alcohol | 65 |

Formulation Example 5

| | |
|---|---|
| Compound No. 5 | 30 |
| | (parts by weight) |
| polyoxyethylene nonylphenyl ether (Emulgen 909, mfd. by Kao) | 5 |
| isopropyl alcohol | 65 |

Formulation Example 6

| | |
|---|---|
| Compound No. 1 | 30 |
| | (parts by weight) |
| sodium ligninsulfonate | 2 |
| polyoxyethylene nonylphenyl ether (Emulgen 911, mfd. by Kao) | 5 |
| clay | 38 |
| bacteriocide (Benomyl) | 25 |

Formulation Example 7

| | |
|---|---|
| Compound No. 2 | 30 |
| | (parts by weight) |
| clay | 45 |
| citric acid | 5 |
| polyoxyethylene fatty acid ester | 10 |
| insecticide (Supracid) | 15 |
| potassium nonylphenyl ether sulfate salt (Levenol WZ, mfd. by Kao) | 5 |

Formulation Example 8

| | |
|---|---|
| Compound No. 5 | 20 |
| | (parts by weight) |

-continued

| | |
|---|---|
| clay | 45 |
| polyoxyethylene sorbitan ester (rheodol TW-O-120, mfd. by Kao) | 5 |
| polyoxyethylene nonylphenyl ether | 5 |
| acaracide (Osadan) | 20 |
| Comparative Formulation Example 1 | |
| sodium ligninsulfonate | 2 |
| polyoxyethylene nonylphenyl ether (Emulgen 911, mfd. by Kao) | 5 |
| fine clay powder (mfd. by Kunimine Kogyo) | 68 |
| bactericide (Benomyl) | 25 |
| Comparative Formulation Example 2 | |
| Comparative Compound No. 2 | 30 |
| sodium nonylphenyl ether sulfate (Levenol WZ, mfd. by Kao) | 5 |
| insecticide (Supracid) | 15 |
| fine clay powder (mfd. by Kunimine Kogyo) | 50 |
| Comparative Formulation Example 3 | |
| Comparative Compound No. 1 | 5 |
| polyoxyethylene nonylphenyl ether | 50 |
| fine clay powder (mfd. by Kunimine Kogyo) | 45 |
| acaricide (Osadan) | 20 |

Example 1

10 ml/pot of a spore suspension (10/ml) of *Botrytis cinerea*, exhibiting resistance to bactericides, was applied to young cucumber seedlings at the trifoliate stage. Next, the seedlings were allowed to stand at 25° C. under a relative humidity of 90% for one day. In Test Examples 1 to 5, the biocide activators obtained in the above Formulation Examples 1 to 5 were added to a solution of marketed Benomyl (active ingredient concentration: 250 ppm) in such a manner as to dilute each of the activator 1000-fold. In Test Example 6 and Comparative Test Examples 1 and 2, on the other hand, the dilution was effected in such a manner as to give the content of the active ingredient of Benomyl of 250 ppm. Then, each of the obtained samples was applied in a dose of 5 ml per pot. In Comparative Test Example 3, the procedure of Test Example 1 was repeated except that no Benomyl was added.

Next, the seedlings were allowed to stand at 25° C. under a relative humidity of 85%. After four days, the lesions which had formed on each seedling were counted and the preventive value based on the control group was calculated in accordance with the following equation:

$$\text{preventive value} = \left(1 - \frac{\text{lesion number of test group}}{\text{lesion number of control group}}\right) \times 100$$

Table 2 shows the results.

TABLE 2

| | Biocide activator | | Agrohorticultural bactericide | Active Ingredient content of | | |
|---|---|---|---|---|---|---|
| | Formulation Example | Dilution | Marketed Benomyl Preparation | Benomyl at application (ppm) | Preventive value | Harmful effect |
| Test Example | | | | | | |
| 1 | Formulation Example 1 | 1000-fold | separately added | 250 | 98 | — |
| 2 | Formulation Example 2 | " | " | " | 100 | — |
| 3 | Formulation Example 3 | " | " | " | 98 | — |
| 4 | Formulation Example 4 | " | " | " | 98 | — |
| 5 | Formulation Example 5 | " | " | " | 100 | — |
| 6 | Formulation Example 6 | " | none (contained in preparation) | " | 98 | — |
| Comp. Test Example | | | | | | |
| 1 | Comp. Formulation Example 1 | 1000-fold | none (contained in preparation | 250 | 75 | + |
| 2 | — | — | added | 250 | 67 | — |
| 3 | Formulation Example 1 | 1000-fold | none | 0 | 35 | — |

Example 2

The efficiency of the insecticide (Supracid) was examined by the Chinese cabbage leaf dipping method with the use of *Myzus persica* Sulzer imagines (each lot having 30 imagines) by three times.

The preventive values were determined based on the data of a control group.

In Test Examples 1 to 5, the biocide activators obtained in Formulation Examples 1 to 5 were mixed with a 180 ppm solution of marketed Supracid in such a manner as to dilute each of the activators 1000-fold. In Test Example 6 and Comparative Test Examples 1 and 2, on the other hand, the dilution was effected in such a manner as to give a content of the Supracid active ingredient of 180 ppm. In Comparative Test Example 3, the procedure of Test Example 2 was repeated except no Supracid was added.

Table 3 shows the results.

TABLE 3

| Biocide activator Formulation Example | Dilution | Agrohorticultural insecticide Marketed Supracid Preparation | Active Ingredient content of Supracid at application (ppm) | Preventive value | Harmful effect |
|---|---|---|---|---|---|
| Test Example | | | | | |
| 1  Formulation Example 1 | 1000-fold | separately added | 180 | 100 | — |
| 2  Formulation Example 2 | " | " | " | 100 | — |
| 3  Formulation Example 3 | " | " | " | 100 | — |
| 4  Formulation Example 4 | " | " | " | 100 | — |
| 5  Formulation Example 5 | " | " | " | 100 | — |
| 6  Formulation Example 7 | " | none (contained in preparation) | " | 100 | — |
| Comp. Test Example | | | | | |
| 1  Comp. Formulation Example 2 | 1000-fold | none (contained in preparation added | 180 | 66 | + |
| 2  — | — | separately added | " | 60 | — |
| 3  Formulation Example 2 | 1000-fold | none | 0 | 23 | — |

Example 3

Acaricidal effects were examined in a field, wherein *Panonychus citri* McGregor resistant to marketed acaricide (Osadan) bred, by using three Citrus unshu trees per group.

In Test Examples 1 to 5, the biocide activators obtained in Formulation Examples 1 to 5 were mixed with a 125 ppm solution of the marketed Osadan in such a manner as to dilute each of the activators 1000-fold. In Test Example 6 and Comparative Test Examples 1 and 2, on the other hand, the dilution was effected in such a manner as to give a content of the Osadan active ingredient of 125 ppm. In Comparative Test Example 3, the procedure of Test Example 1 was repeated except that no Osadan was added.

Then 3, 10, 20 and 30 days after the treatment with chemicals, mites on 30 leaves per tree were counted and the preventive value of each group was calculated based on the data obtained in the control lot.

Table 4 shows the results.

TABLE 4

| Biocide activator Formulation Example | Dilution | Agrohorticultural acaricide Marketed Osadan Preparation | Active Ingredient content of Osadan at application (ppm) | Preventive value | Harmful effect |
|---|---|---|---|---|---|
| Test Example | | | | | |
| 1  Formulation Example 1 | 1000-fold | separately added | 125 | 99 | — |
| 2  Formulation Example 2 | " | " | " | 99 | — |
| 3  Formulation Example 3 | " | " | " | 97 | — |
| 4  Formulation Example 4 | " | " | " | 100 | — |
| 5  Formulation Example 5 | " | " | " | 100 | — |
| 6  Formulation Example 8 | " | none (contained in preparation) | " | 98 | — |
| Comp. Test Example | | | | | |
| 1  Comp. Formulation Example 1 | 1000-fold | none (contained in preparation | 125 | 65 | + |
| 2  none | — | separately added | " | 46 | — |
| 3  Formulation Example 3 | 1000-fold | none | 0 | 38 | — |

Example 4

The effect of the biocide activator of the present invention on plants was examined in the following manner. Namely, cucumber, kidney bean, tomato, eggplant and strawberry plants were grown in a greenhouse and the effect of the compound on fruits and leaves of these crops was examined.

Table 5 shows the results.

TABLE 5

| Test Example | Dilution | Test Crop cucumber | kidney bean | tomato |
|---|---|---|---|---|
| compound of the | | | | |

TABLE 5-continued

| Test Example | Dilution | Test Crop | | |
|---|---|---|---|---|
| | | cucumber | kidney bean | tomato |
| invention | | | | |
| 1 | ×500 | 0 | 0 | 0 |
| 2 | ×500 | 0 | 0 | 0 |
| 3 | ×500 | 0 | 0 | 0 |
| 4 | ×500 | 0 | 0 | 0 |
| 5 | ×500 | 0 | 0 | 0 |
| Comparative Compound | | | | |
| 1 | ×500 | 2 | 4 | 2 |
| 2 | ×500 | 3 | 4 | 3 |

Criteria for Harmful Effect
0 = none
1 = slightly browning
3 = browning
4 = major browning
5 = major browning and partly dead

Results

As the Examples 1 to 4 show, the biocide activator of the present invention apparently enhances biocidal effects without any adverse effects on crops.

What is claimed is:

1. A biocide composition which comprises a biocidally effective amount of a biocide which is hexakis (2-methyl-2-phenylpropyl) distannoxane, and an effective amount of a biocide activator having the formula (I):

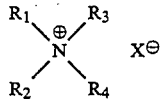

wherein $R_1$ represents linear alkyl having 20 to 40 carbon atoms; $R_2$ and $R_3$ are independently selected from the group consisting of

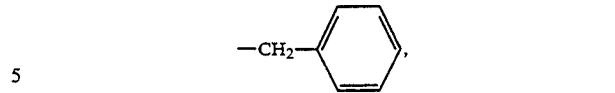

alkyl having 1 to 4 carbon atoms and hydroxyalkyl having 2 to 4 carbon atoms; $R_4$ is alkyl having 12 to 30 carbon atoms, and wherein $R_1$ contains greater than two carbon atoms more than $R_4$; and counter-ion $X^{\ominus}$ is an anion of a halogen acid a polyoxyethylene alkylphenylether sulfate, a polyoxyethylene tribenzylphenylether sulfate or a sulfuric acid ester having an alkyl group of 10 or fewer carbon atoms.

2. The biocide composition according to claim 1, wherein said biocide is present in an amount of 1 to 50% by weight.

3. The biocide composition according to claim 1, wherein said biocide activator is present in an amount of 0.005 to 60% by weight.

4. The biocide composition according to claim 1, wherein said biocide activator is a compound having formula (I) in which $R_1$ contains 4 to 12 more carbon atoms than $R_4$.

5. The biocide composition of claim 1, wherein counter-ion $X^{\ominus}$ is selected from the group consisting of $Cl^-$, $I^-$, $Br^-$, alkylsulfate, polyoxyethylene alkylsulfate, polyoxyethylene alkylphenylether sulfate, alkylbenzene sulfate, naphthalene sulfate, alkylnaphthalene sulfate and polyoxyethylene tribenzylphenylether sulfate.

6. The biocide composition of claim 1, further comprising a biocidally acceptable (i) salt selected from the group consisting of metal salts of carboxylic acids, metal salts of phosphoric acid compounds and inorganic salts; (ii) surfactant; (iii) thickening agent; (iv) acid selected from the group consisting of acetic acid, a butyric acid, capric acid, caproic acid, succinic acid, lactic acid, malonic acid, citric acid, gluconic acid, glutaric acid, phosphoric acid, tripolyphosphoric acid, hexametaphosphoric acid, methanesulfonic acid, sulfonic acid, hydrochloric acid and nitric acid; or (v) carrier.

7. A biocidal method comprising applying to a locus in need of biocidal treatment an effective amount of a biocide composition according to claim 1.

* * * * *